US009241853B2

(12) United States Patent
Carlson et al.

(10) Patent No.: US 9,241,853 B2
(45) Date of Patent: Jan. 26, 2016

(54) MULTIPLE PLY MANAGED FRICTION MATERIAL SURFACE WITH SMOOTH BONDED SEAMS

(71) Applicant: Tamarack Habilitation Technologies, Inc., Blaine, MN (US)

(72) Inventors: J. Martin Carlson, Mora, MN (US); Adam Erickson, St. Paul, MN (US); Mark N. Manzella, Maplewood, MN (US); Mark J. Payette, Lino Lakes, MN (US)

(73) Assignee: TAMARACK HABILITATION TECHNOLOGIES, INC., Blaine, MN (US)

( * ) Notice: Subject to any disclaimer, the term of this patent is extended or adjusted under 35 U.S.C. 154(b) by 164 days.

(21) Appl. No.: 13/975,807

(22) Filed: Aug. 26, 2013

(65) Prior Publication Data

US 2013/0340772 A1 Dec. 26, 2013

Related U.S. Application Data

(63) Continuation-in-part of application No. 13/262,081, filed as application No. PCT/US2010/031695 on Apr. 20, 2010, now Pat. No. 8,919,347.

(60) Provisional application No. 61/171,863, filed on Apr. 23, 2009, provisional application No. 61/692,742, filed on Aug. 24, 2012.

(51) Int. Cl.
*A61F 13/14* (2006.01)
*A61G 5/10* (2006.01)
*A61G 7/057* (2006.01)

(52) U.S. Cl.
CPC .............. *A61G 5/1043* (2013.01); *A61G 7/057* (2013.01)

(58) Field of Classification Search
CPC combination set(s) only.
See application file for complete search history.

(56) References Cited

U.S. PATENT DOCUMENTS 2,641,257 A 6/1953 Rutledge
4,571,960 A 2/1986 Hursh et al.

(Continued)

FOREIGN PATENT DOCUMENTS

JP 2003024201 A 1/2003
WO 0025642 A1 5/2000

(Continued)

OTHER PUBLICATIONS

PCT International Search Report, Dec. 30, 2010.

(Continued)

*Primary Examiner* — Ophelia A Hawthorne
(74) *Attorney, Agent, or Firm* — Westman, Champlin & Koehler, P.A.; Z. Peter Sawicki; Amanda M. Prose

(57) ABSTRACT

A substantially smooth, seamless managed friction material surface and apparatus for placement on a support surface between the support surface and a living being for preventing abrasion or decubitus ulcers in a living being. The managed friction material surface comprises a plurality of plies having a smooth side and a first, high friction zone and second, low friction zone. At least one adhesive ply is interposed partially between adjacent plies; and the plies are selectively bonded to form adjacent frictional zones of high and low friction. Unbonded plies are allowed to move substantially freely with respect to one another thus providing a lower friction zone. The apparatus comprises the managed friction material surface such that the bonded zone is configured for positioning remote the bony prominence and the unbonded zone for positioning proximate the bony prominence, seamlessly occupying different areas on the same side of the material surface.

18 Claims, 14 Drawing Sheets

(56) References Cited

U.S. PATENT DOCUMENTS

| | | | | |
|---|---|---|---|---|
| 4,572,174 | A | 2/1986 | Eilender et al. | |
| 4,615,188 | A | 10/1986 | Hursh et al. | |
| 4,843,844 | A | 7/1989 | Hursh et al. | |
| 4,873,982 | A | 10/1989 | Morrison | |
| 5,084,928 | A * | 2/1992 | Skillington | 5/490 |
| 5,127,119 | A | 7/1992 | Rogers | |
| 5,638,558 | A | 6/1997 | Moore | |
| 5,787,523 | A * | 8/1998 | Lindberg | 5/81.1 HS |
| 5,799,333 | A | 9/1998 | McGarry et al. | |
| 6,108,820 | A | 8/2000 | Bernhardt | |
| 6,145,132 | A | 11/2000 | Towner | |
| 6,633,830 | B2 | 10/2003 | Chen et al. | |
| 6,918,140 | B1 | 7/2005 | Cooper | |
| 7,213,420 | B2 | 5/2007 | Lynch et al. | |
| 7,281,549 | B2 | 10/2007 | Metzger | |
| 2004/0022426 | A1 * | 2/2004 | Carbone et al. | 382/141 |
| 2004/0123391 | A1 | 7/2004 | Call | |
| 2005/0125901 | A1 | 6/2005 | Nichols | |
| 2005/0208854 | A1 * | 9/2005 | Sadato et al. | 442/289 |
| 2007/0220673 | A1 | 9/2007 | Nichols | |
| 2007/0277282 | A1 | 12/2007 | Sheppell | |
| 2008/0121305 | A1 | 5/2008 | Metzger | |
| 2008/0264512 | A1 | 10/2008 | Metzger | |

FOREIGN PATENT DOCUMENTS

| | | | |
|---|---|---|---|
| WO | 2004050002 | A1 | 6/2004 |
| WO | 2010039524 | A2 | 4/2010 |
| WO | 2010123857 | A8 | 10/2010 |

OTHER PUBLICATIONS

UK Examination Report; GB1117730.0; Dec. 19, 2012.

Baby Gadget retail listing, undated, see the A-Z duvet cover, accessed Jan. 14, 2014. available from http://www.babygadget.net/2006/11/b__is__for__bedtime__with__the__az__d.php.

All Things Infant retail listing, undated, see the Jole Alphabet Cot Duvet Set, accessed Jan. 14, 2014. available from http://www.allthingsinfant.co.nz/webapps/p/93835/266071/954903.

Heirloom Linens retail listing, undated, see the E-Z Peasy Kids Bedding, accessed Jan. 14, 2014. available from http:// www.heirloomlinens.com/product.aspx?ProductID=960&deptid=64&ProceCat=1&Lang=EN-US&SID=6c4acaa9-dfc2-495c-b140-479fd3c41255.

Etsy retail listing, undated, see the Classic Alphabet Pillow Cover, accessed Jan. 14, 2014. available from http://www.etsy.com/listing/73817948/classic-alphabet-pillow-cover-blue-and.

Art Fire retail listing, undated, see the Monogram Letter Pillow Cover, accessed Jan. 14, 2014, available from http://www.artfire.com/ext/shop/product__view/comfyheaven/7745040/monogram__letter__pillow__cover__black__and__white__18__inch__-ns01.

Running With Scisors craft instruction, undated, see the Ampersand Decor Pillow tutorial, accessed Jan. 14, 2014, available from http://www.running-w-scissors.com/2011/03/ampersand-decor-pillow.html.

Examination Report for GB1117730.0, Jan. 17, 2014.

* cited by examiner

MULTIPLE PLY MANAGED FRICTION MATERIAL SURFACE WITH SMOOTH BONDED SEAMS

CROSS-REFERENCE TO RELATED APPLICATIONS

The present application is a continuation-in-part of currently pending U.S. patent application Ser. No. 13/262,081, filed Sep. 29, 2011, now U.S. Pat. No. 8,919,347, which is a Section 371 National Stage Application of International Application No. PCT/US2010/031695 filed Apr. 20, 2010, and published as WO 2010/123857 A2 on Oct. 28, 2010, which claims priority to U.S. provisional patent application Ser. No. 61/171,863, filed Apr. 23, 2009, the content of which is hereby incorporated by reference in its entirety. The present application also claims the benefit of U.S. provisional patent application Ser. No. 61/692,742, filed Aug. 24, 2012, the content of which is hereby incorporated by reference in its entirety.

BACKGROUND

Typically, paraplegics, amputees and others with disabilities or who are otherwise bedridden or require permanent or prolonged use of wheel chairs or other support surfaces often have compromised skin integrity. Their skin is subject to long periods of interface with support surfaces such as beds, head rests, wheelchairs or artificial limbs, and is extremely sensitive to the surface qualities of these supports, and specifically the portions that contact their body.

Abrasion and ulceration of skin is commonly caused, and exacerbated, by this prolonged contact. The general population is also susceptible to skin conditions from temporary and prolonged contact with certain fabric materials, but abrasion and ulceration are especially troublesome to susceptible populations. These and similar skin conditions cause pain and discomfort and can also lead to infection and other complications.

Persons who are susceptible to skin damage are aware of the risk rough materials cause with respect to chafing, abrasion and decubitus ulcers. These aware populations often select material surfaces that are as smooth as possible and free from abrasion causing items such as sewn seams, especially proximate areas of vulnerable skin. For example many paraplegics avoid wheelchair cushion covers with sewn seams that could cause abrasion and ulceration.

Sewn seams can lead to chafing by their roughness acting directly upon the skin. However, sewn seams can also increase the coefficient of friction of a surface, in effect gripping the skin. The sewn seam and associated increase in friction causes skin and the tissue below to experience shear stresses that would not be present in a more smoothly constructed seam. These shear stresses can lead to tissue damage such as decubitus ulcers. It should be understood chafing, abrasion, ulceration and skin damage are all risks associated with sewn seams.

Presently, various fabrics, materials, coatings and/or cushions are used to cover support surfaces as required by injury or illness. Many of these items are formed by sewing materials or otherwise stitching such that seams are formed. The seams are generally rough, abrasive or otherwise not smooth. Many users believe that stitching, and the resulting seam, can threaten skin integrity by abrasion and thus would prefer a lack of stitched seams in contact with their body. This aversion to stitching is especially relevant in areas of high contact pressure between the user's body and a support surface.

It is problematic that sewn seams are used to join multiple panels or plies of these materials. However these seams are necessary in the construction of cushion covers, bedding, medical devices, garments and other items, having multiple panels or plies of material. The seams described above can be beneficial by supporting the use of multiple panels or plies to create a material surface with zones of high and low friction. A material surface with zones of low friction and high friction has the potential to decrease the likelihood of discomfort, abrasion and ulceration in many users. Unfortunately the use of sewn seams on these material surfaces often forms a surface that is rough or abrasive and causes discomfort for users and may result ultimately in ulcers or abrasions.

The costs of treating pressure ulcers in the United States alone are staggering. More than 2.5 million pressure ulcers are treated each year in the United States with treatment costs as high as $11 billion. Prevention of pressure ulcers would not only reduce pain and suffering but also medical costs and lost work hours.

Presently, it is difficult to sew plies of fabric that are extremely low in friction, and thus feed poorly through a sewing machine. Such low friction plies tend to slide around in the sewing machine and cause wrinkling and uneven sewn seams in the final product. These very low friction materials are hard to sew properly even using the best sewing machine feeding mechanisms such a walking foot or upper feed dog used in combination with a lower feed dog.

Some aspects of bonding fabrics or dissolving certain materials to aid sewing are known in the prior art. One prior art technique is the use of dissolvable paper to stiffen light materials before sewing. The paper is then dissolved in water after sewing is complete. Unfortunately this technique is not suitable for many situations as fibers are left behind, such as the case where fibers are trapped under stitching or between material. Prior art dissolvable adhesives are illustrated in U.S. Pat. No. 5,094,912 (where an acrylic adhesive is dissolved using a 2% aqueous soda solution), EP 2031032B1, WO2001/046329A1, EP2120228A2, and U.S. Pat. No. 8,361,616 B2.

Unfortunately sewn seams that contact a user's anatomy, either directly or through intervening layers, are often perceived by the user as rough and posing a risk of causing abrasion or ulceration. Many prior art material surfaces that are commonly part of the construction of cushion covers, bedding, garments and medical devices, have sewn seams proximate critical areas of a user's anatomy. For example, prior art shorts often require a sewn seam proximate the ischial tuberosities to assure that the garment fits a user appropriately. Material surfaces wishing to incorporate zones of low friction often have sewn seams on the perimeter of the high and/or low friction zones. These seams detract from the smooth and abrasion free surface desired by users.

BRIEF SUMMARY OF THE INVENTION

This disclosure relates to a bonded managed friction material surface is disclosed which can be used to help prevent abrasion and ulceration. These bonded managed friction material surfaces are generally made from multiple panels or plies. Due to a unique construction with uniform bonded seams, the managed friction material surface is mostly smooth and free from abrasion causing seams. This managed friction material surface is generally suitable for contact with a user's anatomy with or without intervening layers.

This disclosure also relates to a substantially smooth managed friction material surface for preventing abrasion or decubitus ulcers in a living being. The managed friction material surface comprises a first and second ply of material, each having a smooth side. The managed friction material surface comprises a first zone and a second zone, such as a high and low frictional zone, wherein the plies are selectively bonded to form the first frictional zone having greater friction than the second zone. The plurality of plies remain unbonded in the second frictional zone, the zone positioned proximate the first frictional zone and the second frictional zone having lower friction. The second frictional zone also comprises two plies of material that are allowed to move substantially freely with respect to one another in the second frictional zone.

This disclosure also relates to a substantially smooth managed friction material surface for preventing abrasion or decubitus ulcers in a living being, said managed friction material surface comprising a plurality of plies, each ply having a smooth side, a first and second frictional zone and at least one adhesive ply interposed partially between adjacent plies. The plurality of plies are selectively bonded at the adhesive ply to form the first frictional zone of higher friction. The plurality of plies then remains unbonded proximate the first frictional zone to form the second frictional zone of lower friction. The adjacent plies are allowed to move substantially freely with respect to one another in the second frictional zone of lower friction.

This disclosure also relates to an apparatus for placement on a support surface between the support surface and a living being, the living being having a bony prominence. The apparatus comprises a substantially smooth and seamless material surface having a bonded zone having a high coefficient of friction and configured for positioning remote the bony prominence. The apparatus further comprises an unbonded zone adjacent the bonded zone, the unbonded zone having a low coefficient and configured for positioning proximate the bony prominence. Further, the bonded zone and the unbonded zone occupy different areas on the same side of the material surface and no sewn seam exists on the material surface between the adjacent zones.

DETAILED DESCRIPTION

Figure 1:
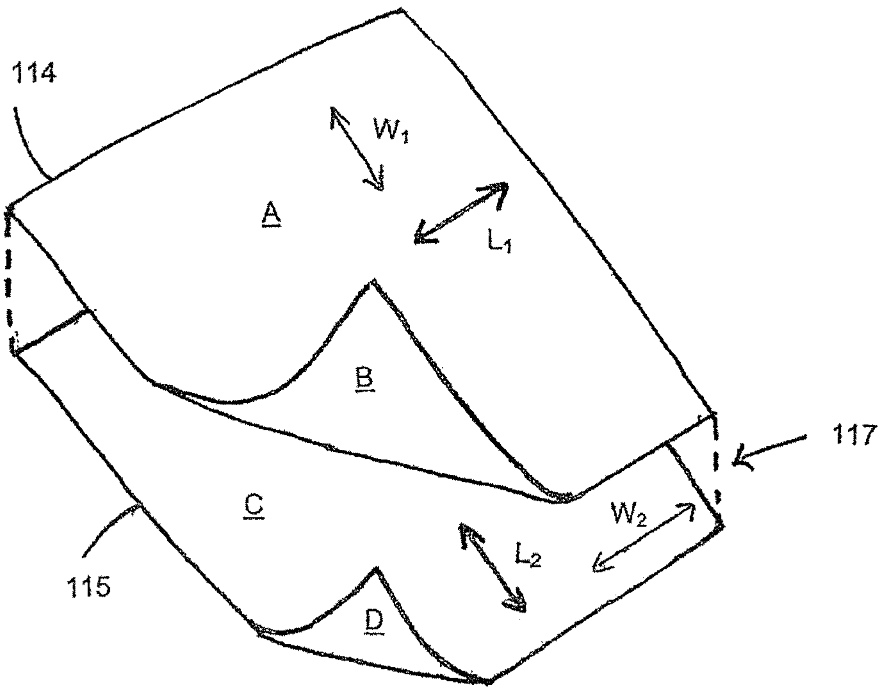
FIG. 1 is an exploded perspective view of a two ply low friction interface.

The present invention includes a material surface designed to reduce friction, shear and abrasive seams. The present device mitigates shear by increasing the "slipperiness" (i.e., reducing the coefficient of friction (COF)) in an interface between the skin and a surface. If defining Lf as a friction load, Lp as a load perpendicular to a skin surface (pressure type load), and COF as a coefficient of friction of a "slipperiest" interface, then Lf cannot be greater than Lp×COF, i.e., Lf≤Lp×COF.

There are several reasons to focus on shear reduction. First, in relative terms, shear is more destructive of tissue integrity than pressure. Second, in some instances, it may be easier to manage friction and shear than it is to manage pressure. Third, most efforts to control peak pressure involve foam materials, which accelerate ulcer formation by reducing breathability (i.e. impeding heat dissipation and evaporation).

Managing friction and shear does not mean eliminating all friction. Not all friction is bad. In fact, some friction is often essential. For example frictional forces are often used to prevent a user from sliding forward in a chair or out of a bed. What is meant by managed friction material surface is a material surface whose fiction characteristics have been uniquely tailored for interface with a living being. The managed friction material surface could have both zones of high friction and zones of low friction. Zones of low friction should be located proximate vulnerable areas of the user's anatomy to help prevent abrasion and ulceration. High friction zones should be located proximate more tolerant areas of a users' anatomy to help with positioning or retention of the user and/or material surface.

In the case of a seat cushion, higher friction areas would typically be located remote from bony prominences such as under the fatty areas of a user's thighs. The managed friction material surface of the present invention is often configured to oppose a user's anatomy such that it provides a frictional interface with another surface such as a bed mattress. In one example, the managed friction material surface is configured such that a low friction zone opposes an area of sensitive skin. The low friction zone protects the area of sensitive skin from rubbing and abrasion against the bed mattress.

Configuring the managed friction material surface often results in a material surface with boundaries between zones of high friction and zones of low friction. The boundaries between the zones of low friction and zones of high friction could comprise sewn seams. In the present invention these boundaries are bonded. Bonding can reduce any negative impact on a user generally attributed to a sewn seam, make sewing easier and/or used to reinforce a sewn seam.

The present invention generally includes a managed friction material surface 111. The managed friction material surface 111 comprises an adhesive ply 116 used to selectively bond a plurality of plies of material, generally at least a first ply 114 and a second ply 115, the plurality of plies comprising materials capable of forming a low friction interface 117. Bonded areas 129 of the surface 111 generally form high friction zones 113, wherein unbonded areas 126 form low friction zones 112. Thus, selectively bonding the materials form not only a smooth seam that supports and ensures skin integrity, but allows precise placement of low and high friction zones to a finished product. Further, the bonding may cover a large surface area to form substantially a large, continuous high friction zone 113, or may be done selectively in small, targeted areas or small strips to provide various areas of low friction 112. Bonding is used to construct a managed friction material surface 111 that substantially reduces and even eliminates the negative effects of stitched or similarly attached seams upon a user.

Figure 2:
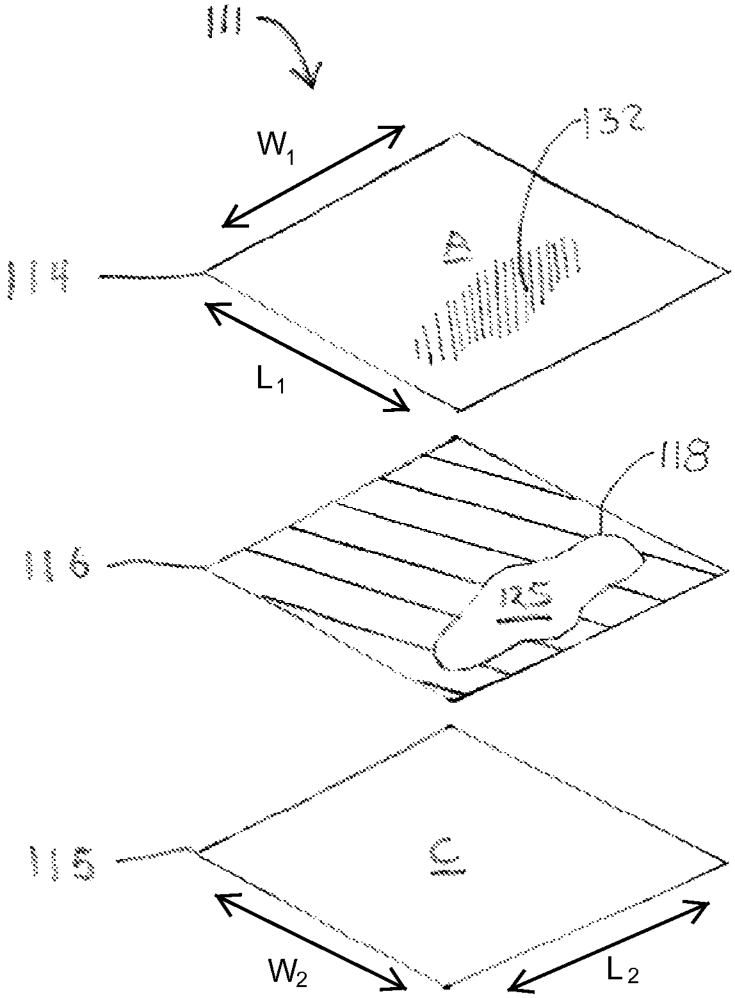
FIG. 2 is an exploded perspective view of a further embodiment of the two ply low friction interface.
Figure 3:
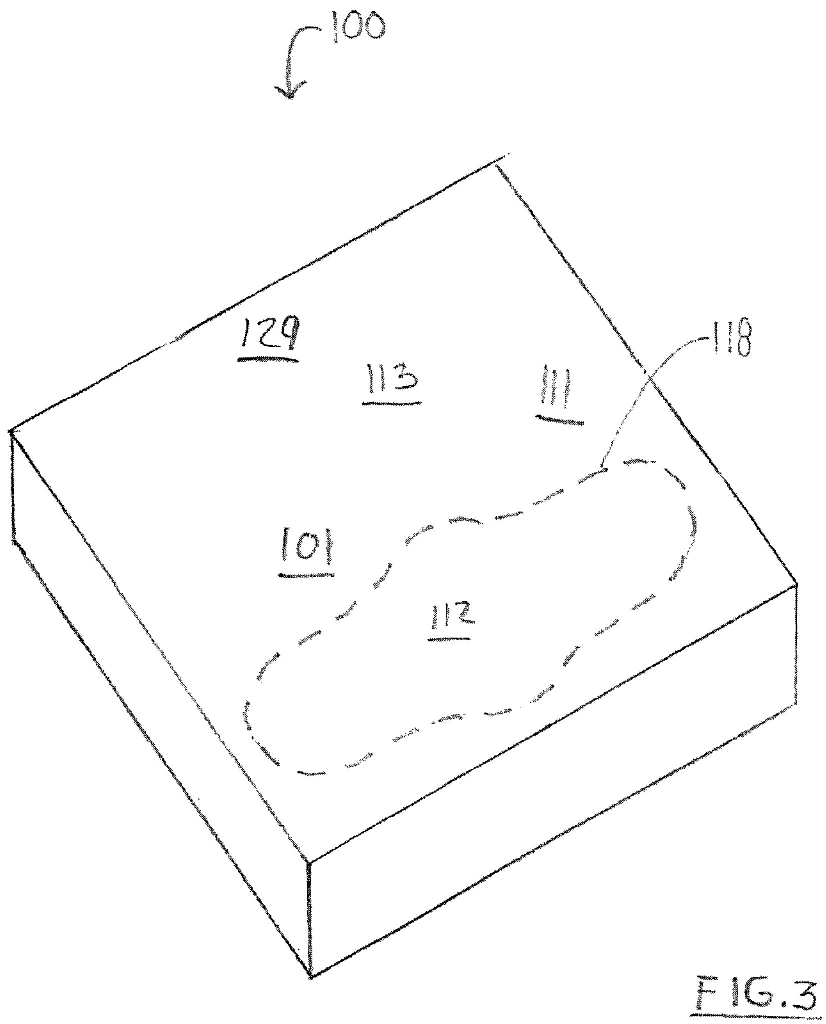
FIG. 3 is a perspective view of a further embodiment of present invention.

In one exemplary embodiment, as illustrated generally in FIGS. 1-3, a cover 100 incorporates the zone of low friction 112, the zone of high friction 113, a bonded construction and a substantially smooth surface 101. The cover 100 comprises the smooth managed friction material surface 111, which comprises materials similar to those used on wheelchair cushions and various other support surfaces.

Figure 4:
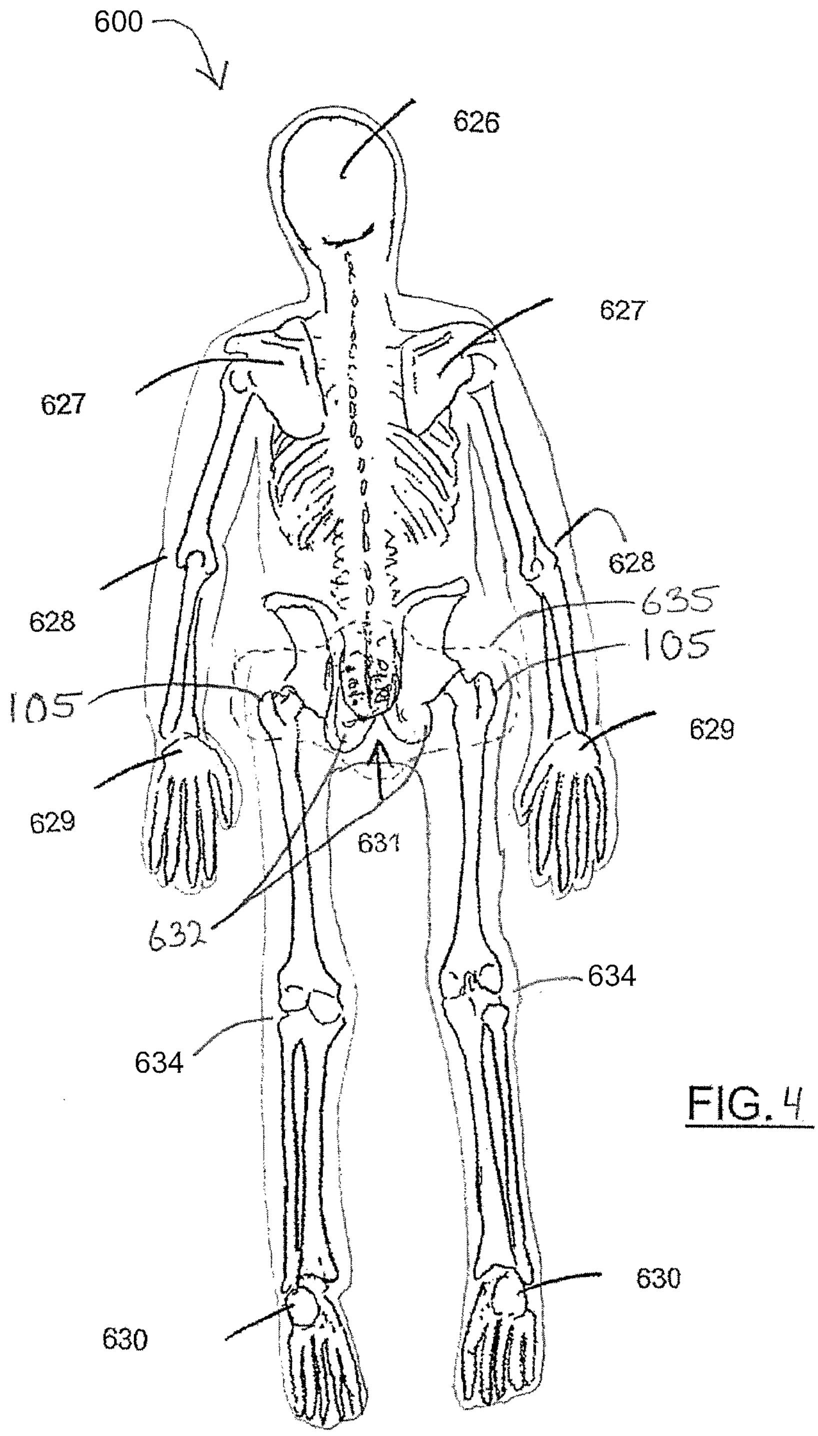
FIG. 4 is a front view of a user.

As further illustrated in FIGS. 3 and 4, the smooth surface 101 is configured to contact a user's anatomy 600 either with or without intervening layers. Some areas of the user's anatomy 600 can better withstand the effect of friction and shear than others. Generally, the more tolerant areas are located remote from bony prominences such as parts of the gluteal regions and the undersides of the thighs. For purposes of support surface design, for use when in a sitting position, the area of greatest concern for decubitus ulcer formation can be identified.

Figure 5:
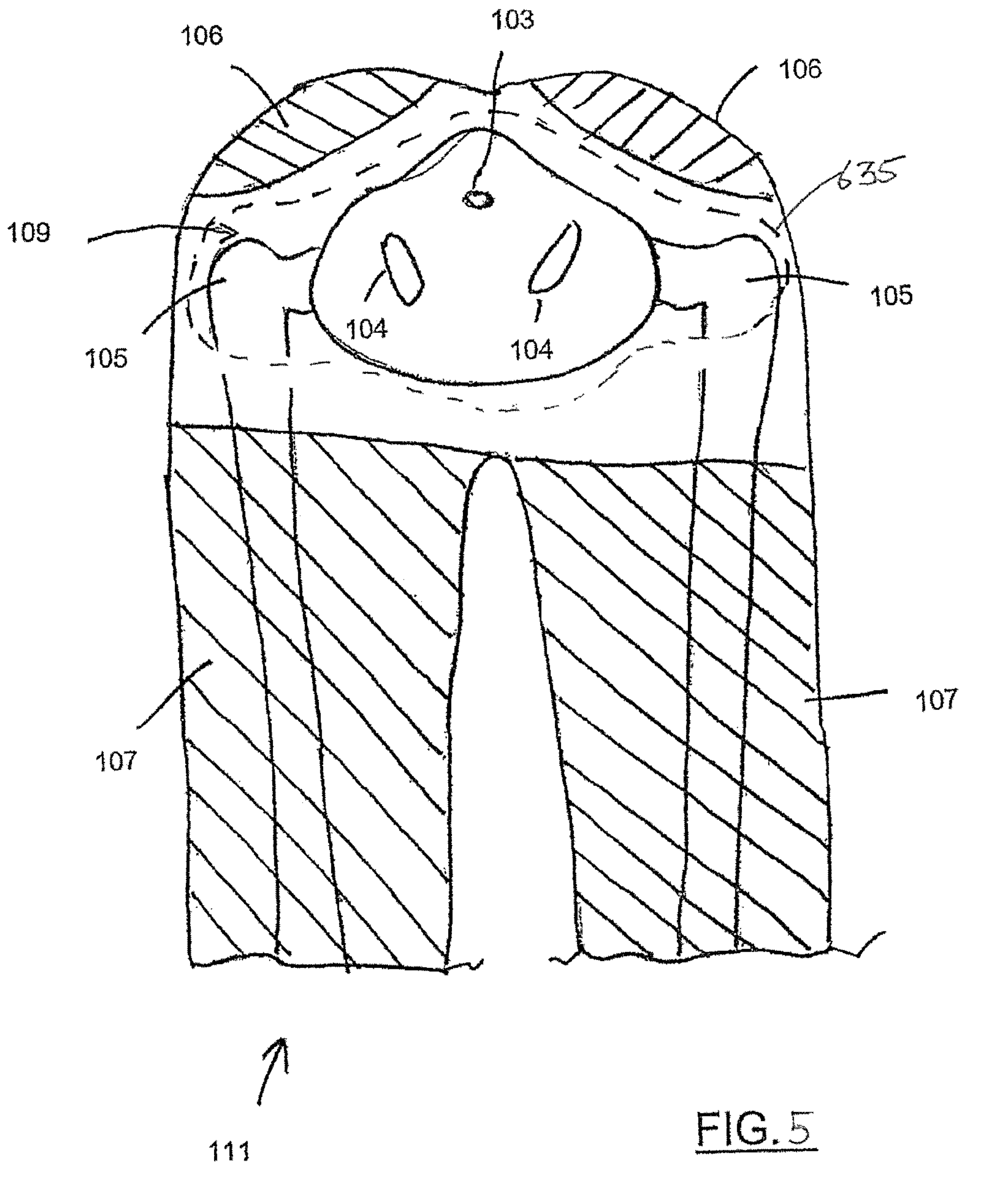
FIG. 5 is a bottom, cross-section view of the user.

As illustrated generally in FIG. 5, if one were to draw a line around the bony prominences, the area within the dotted line can be considered the primary area of tissue vulnerability 635 for most sitters. Managing friction and shear in this area of tissue vulnerability 635 for most sitters can be critical. The design of cover 100 can take into account the susceptibility of various regions of the body to skin trauma. The cover 100 will then have zones of low friction 112 and zones of high friction 113 placed with the users anatomy in mind. The zones of low friction zones 112 can be positioned opposite areas of vulnerable tissue. The zones of high friction 113 can be positioned opposite more tolerant areas of a user's anatomy.

The high friction zones 113 could be positioned opposite parts of the body more distant from bony prominences such as parts of the gluteal regions 106 and the undersides of the thighs 107. Positioning high friction zones 113 away from bony prominences has advantages. First, areas more remote from bony prominences are typically less susceptible to the formation of decubitus ulcers because more tissue can dissipate shear forces. Second, areas remote from bony prominences can serve to support the body of user 600 and keep them well-positioned on cover 100.

For example, friction against the undersides of the thighs 107 can prevent the body of user 600 from sliding forward on the cushion cover 100. Third, the higher friction zone 113 can be on a front part 129 of cover 100, this can serve as a less slippery location on which to place a hand (or place a transfer board) when the user 600 is re-positioned on or transferred on or off the cushion cover 100. In this embodiment the perimeter 118 of low friction zone 112 corresponds generally to the shape of the area of tissue vulnerability 635. In other embodiments or on other devices the areas of low friction 112 may be shaped differently, for example to protect other areas of vulnerable tissue.

The COF for an interface between two surfaces can be determined. The requirement for having two surfaces to determine a coefficient of friction is often ignored in common language; for example Teflon® is often said to have a low coefficient of friction. What is meant when Teflon® is said to have a low coefficient of friction is that Teflon®, when paired with other common materials, generally exhibits a low coefficient of friction. This does not mean that the interface between Teflon® and all other materials has a low coefficient of friction. When discussing the low friction zone 112, what is meant is a low friction interface generally exists in that zone. When discussing the high friction zone 113, what is meant is a high friction interface generally exists in that zone. What is meant by a single material having a coefficient of friction is a material that generally exhibits such a coefficient of friction when interfaced with other common materials well known in the art.

As illustrated in FIG. 1-3, the low friction zone 112 generally comprises low friction interface 117 and can be formed in a variety of ways. For example an interface of specialty fabrics could be utilized to create the low friction zone 112. While most fabrics form a relatively high friction interface, when properly mated, certain fabrics are then allowed to slide freely against one another, which forms a very low friction interface. The low friction zone 112 can also be formed by using an elastic-type material. The material surface 111 may comprise various different fabrics depending on the needs of the user along with other environmental concerns, and will depend on the requirements of the low friction fabric interface 117. One suitable fabric for both plies 114 and 115 is Style 480 distributed by Cooper Fabrics of Norwood, Mass. Style 480 is a three-bar knit fabric consisting of 85%, 40 denier semi dull nylon and 15%, 140 denier spandex.

The second ply 115 and the adhesive ply 116 are bonded to form smooth surface 101 of cover 100. The first ply 114 has a side A and a side B. The first ply 114, with side A facing up, can be sized to fit cushion cover 100. The second ply 115 is sized substantially similarly to the first ply 114. The second ply 115 has a side C and a side D. Side B of first ply 114 is a bottom side of the first ply 114. Side C is a topside of the second ply 115, which can form a low friction fabric interface 117. The two plies 114, 115 should move relatively freely in relation to each other to create the low friction interface 117. Depending on material selection and environmental conditions, a coefficient of friction of interface 117 may be as low as 0.15.

To form the interface 117, the plies 114, 115 are oriented with respect to one another in the following way: First, sides B and C should face each other as described above. When using the Style 480 fabric, sides B and C are the technical backsides of the fabric, the technical backsides are preferably a shiny side of each fabric, such that the shiny sides of the two plies 114, 115 are facing one another. Thus, a length L1 of the first ply 114 and a length L2 of the second ply 115 should be arranged to be perpendicular with respect to one another, as illustrated in FIG. 1. The lengths L1 and L2 of the first ply 114 and the second ply 115 are in a machine direction and are referred to also as the machine direction. The machine direction can be defined as the direction parallel to the forward movement of material through the knitting or weaving machine. When Style 480 is used, the machine direction will be the same as the direction of greatest stretch. When arranged as discussed previously, and allowed to move relatively freely with respect to one another, the low friction fabric interface 117 demonstrates a very low COF. By comparison, dull sides of the two plies 114 and 115, sides A and D respectively, are of relatively high friction when interfaced with other common material surfaces.

The lengths L1 and L2 of the plies 114, 115 do not have to be arranged precisely perpendicular to achieve a low friction fabric interface. When in use, it is foreseeable that the plies 114 and 115 may slide out of a perpendicular relationship. The closer the lengths L1 and L2 of the plies 114 and 115 remain perpendicular to one another, the lower the coefficient of friction will result.

In this embodiment the plies 114 and 115 of the smooth managed friction material surface 111 are selectively joined by bonding. In this embodiment, the first ply 114 is selectively bonded to the second ply 115 by manipulation of the adhesive ply 116. The adhesive ply 116 comprises a dry melt adhesive, specifically Spunfab PA1008, however any suitable adhesive form may be used. The adhesive ply 116 is cut to a desired size and shape. The shape of the adhesive ply 116 determines the shape of the low friction area. The adhesive ply 116 is interposed between the first ply 114 and second ply 115. Heat bonding is then used to secure the layers. More specifically, the bonding typically occurs when the first ply 114, second ply 115 and interposing adhesive ply 116 are pressed in a heat press such as a Geo Knight DC16AP. The pressing temperature and time may vary, but generally heat bonding at 325 degrees F. requires approximately seven (7) seconds of pressing. The exact pressing temperature and time may vary slightly and are typically determined by pressing several samples and checking bond quality.

The adhesive or bonding agent of adhesive ply 116 may alternatively be applied to a desired area of each or a single ply 114, 115 with a spray nozzle and mask, by screen printing, or by brushing. The adhesive is placed between the layers, or in the case of a contact adhesive, on each layer and the layers are bonded together. Further, the adhesive used is a flexible adhesive. The adhesive ply may further comprise a chemically soluble, yet water-proof adhesive, as the assembled and bonded material surface 111, and thus cushion 100 may be subject to high moisture when in use.

In utilizing screen-printing to secure the first ply 114 and the second ply 115, one or more adhesive plies 116 are used. Adhesive ply 116 is applied to side B of the first ply 114 and/or side C of the second ply 115 by a screen printing process. The screen printing process may include conventional photoresist mask methods, or other suitable methods wherein adhesive is screen-printed on areas corresponding to the high friction zone 113. The first ply 114 and the second ply 115 are then bonded using the screen-printed adhesive, the details of bonding will vary by type of adhesive used. In this embodiment, common screen printable heat cured adhesives are used such that the bonding process is performed in a heat press at approximately 320 degrees Fahrenheit.

Selectively bonding the plies 114, 115 can result in more precise placement of the zones of low 112 and high 113 friction. As further illustrated in FIG. 6, the interposing adhesive ply 116 additionally comprises an area of adhesive removal 125. The area of adhesive removal 125 is an area wherein generally no adhesive is present. The first ply 114 and the partial second ply 119 remain un-bonded proximate the area of adhesive removal 125 and are allowed to move relatively freely with respect to one another in the areas where they are not bonded. The adhesive ply 116 may further comprise various configurations and/or shapes or strips by varying the size and shape of the partial second ply 119 or the areas of adhesive removal 125. The cushion cover 100 utilizing the managed friction material surface 111 will then comprise a plurality of high friction zones 113 and/or low friction zones 112. The elasticity of Style 480 facilitates this relatively free movement of each ply with respect to one another. As such, this embodiment describes a two-ply, low friction fabric interface 117 of low friction zone 112.

The adhesive ply 116 may also further comprise a radiation or UV curable adhesive, in which case, the adhesive is selectively cured by directing radiation upon the desired areas of bonding only. The uncured adhesive is then removed with a solvent that does not affect the cured adhesive. The thickness of the adhesive ply 116, regardless of these adhesive form used, can be thin or generally approximately 0.011 inches. This thin adhesive ply 116 forms a smooth managed friction material surface 111 and the boundary between the high friction zone 113 and low friction zone(s) 112 is thus substantially smooth with no sewn seams.

In areas where the plies are bonded, first ply 114 and second ply 115 are not allowed to move freely with respect to one another, and the area of high friction 113 is thus formed. The dull side A of the first ply 114 and the dull side D of the second ply 115 are relatively high friction when interfaced with common materials well known in the art such as denim, cotton, various types of foam and similar materials or fabrics.

As such, bonding the first ply 114 and the second ply 115 in only certain targeted areas with a dry melt adhesive creates a very smooth managed friction material surface with zones of high friction 113 and zones of low friction 112. A graphic 132 corresponding to the placement of the low friction zone 112 can be placed on side A of the first ply 114 or side D of the second ply 115 such that the location of the low friction zone 112 is easily visually identifiable to the user of the managed friction material surface 111. Placing of the graphic 132 can be accomplished by any number of methods including but not limited to screen-printing of ink. In this manner a user 600 of a smooth managed friction material surface 111 as included in the construction of cover 100 could easily identify the low friction zone 112 and position areas of tissue vulnerability 635 or other sensitive areas of their anatomy proximate the low friction zone 112.

EXAMPLES

Example 1

Figure 6:
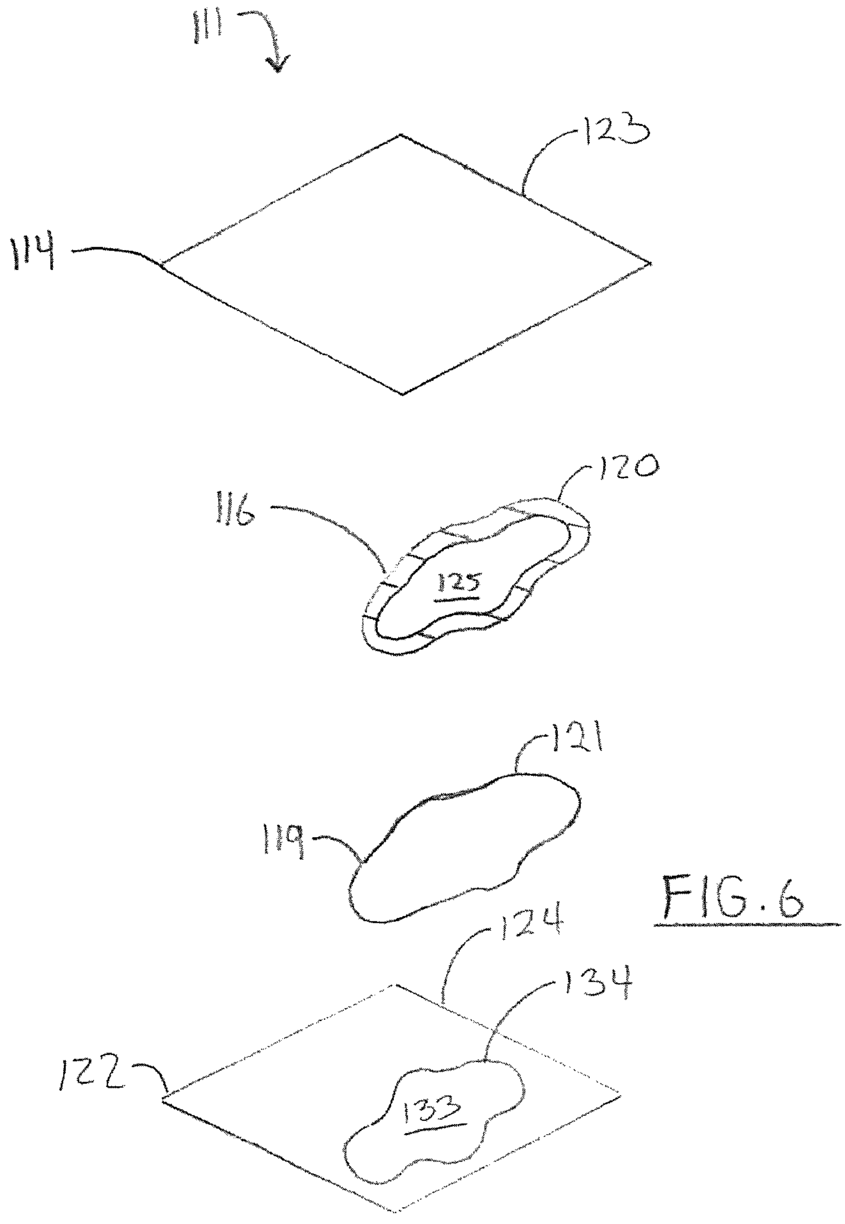
FIG. 6 is an exploded perspective view of an embodiment of the present invention with two plies.

As illustrated in FIG. 6, the managed friction material surface 111 comprises the first ply 114, a partial second ply 119 and the adhesive ply 116. The first ply 114 and partial second ply 119 may comprise Cooper style 480 material, or another suitable material, oriented to form the low friction interface 117 as discussed previously. The thickness of the partial second ply 119 is approximately 0.016 inches. The first ply 114 and partial second ply 119 are bonded with the interposing adhesive ply 116. Adhesive ply 116 comprises adhesive and the area of adhesive removal 125. A heat press bonds the first ply 114 to the partial second ply 119 using the interposing adhesive ply 116 comprising a hot melt adhesive, or suitable alternative. After pressing, the first ply 114 and the partial second ply 119 are bonded where adhesive was present but generally not bonded where adhesive was not present. Thus, the low friction zone 112 is formed where the first ply 114 and the partial second ply 119, which may be smaller in size than the first ply, are not bonded and the plies are allowed to move relatively freely with respect to one another. In this embodiment the adhesive ply 116 is configured with a perimeter 120 of adhesive ply 116 the same as or slightly larger than a perimeter 121 of the partial second ply 119. Adhesive ply 116 is configured to provide an approximately one inch wide bond between the first ply 114 and the partial second ply 119, all around the perimeter 121 of the partial second ply 119, the bond forming the substantially smooth managed friction material surface 111.

Once bonded, the smooth managed friction material surface 111 has zones of high friction 113 and zones of low friction 112 and the need for abrasive sewn seams is eliminated. This smooth managed friction material surface 111 can be used in the construction of a mattress cover or other device.

In the present example, some portion of side B of first ply 114 may contact materials commonly used in bedding or other common devices. Side B of the first ply 114 may form an undesirable low friction interface with some common bedding materials or other material surfaces. As such, a third ply 122 can be bonded to some portion of Side B of first ply 114. The third ply 122 can be a high friction material when interfaced with other common materials. For example the third ply 122 may comprise a thin, low density, foam rubber material. This third ply 122 helps to assure that, generally, a frictional interface will not be formed with side B of the first ply 114 that is lower than desired when interfaced other common materials, such as bedding materials or mattress covers.

Adhesive ply 116 may be used to bond the third ply 122 to the first ply 114. The perimeter 120 of adhesive ply 116 may be large, for example larger than perimeter 123 of first ply 114. Adhesive ply 116 can also bond third ply 122 to first ply 114. The third ply 122 comprises a non-woven material constructed of polyester, or another suitable material or fabric that generally forms a high friction interface with other commonly used bedding materials. Those skilled in the art will appreciate that the third ply may comprise any combination of common high friction materials. The third ply 122 also includes a cutout 133 with a perimeter 134 that is similar to the perimeter 121 of the partial second ply 119. The perimeter 124 of third ply 122 may be similar to the perimeter 123 of first ply 114.

Example 2

Figure 7:
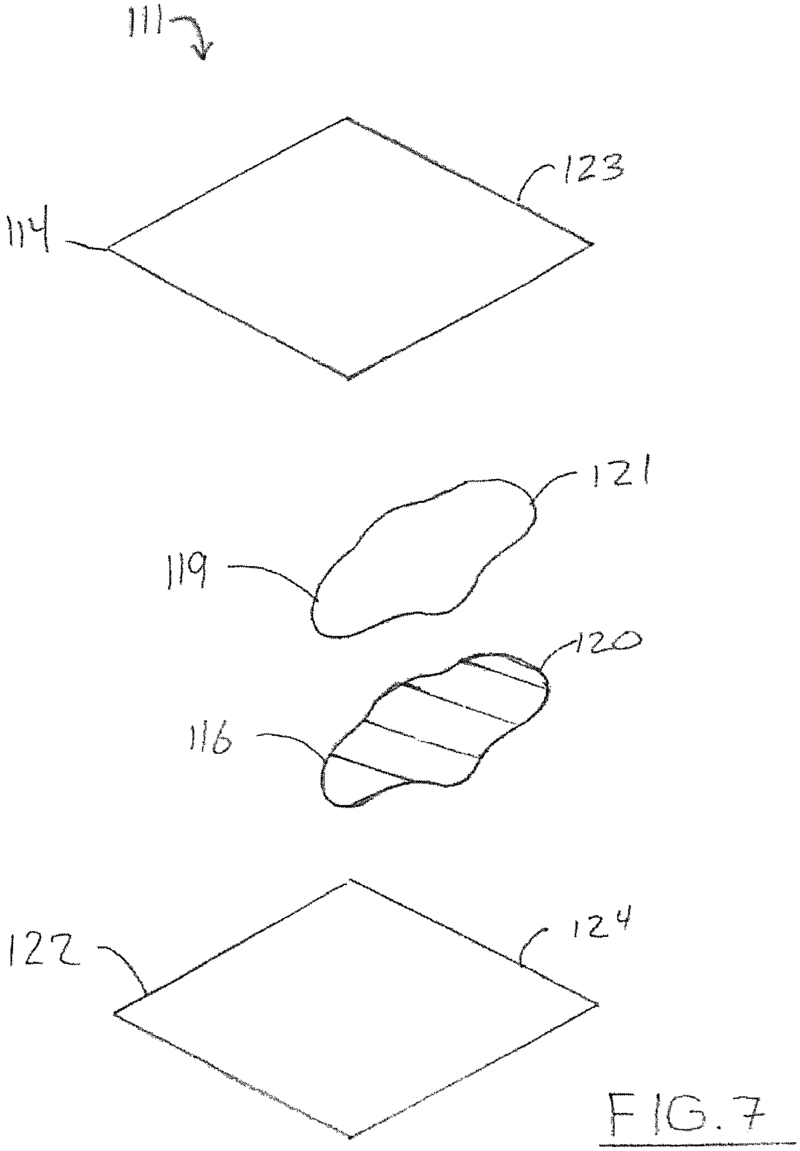
FIG. 7 is an exploded perspective view of an embodiment of the present invention with three plies.

As illustrated generally at FIG. 7, the low friction zone 112 can be created using a material that has a low coefficient of friction against other common materials. One suitable material is polytetrafluoroethylene, however any other generally slippery material may be used. Polytetrafluoroethylene can be used to form interfaces with very low coefficients of friction. The partial second ply 119 comprises Polytetrafluoroethylene. The perimeter 121 of partial second ply 119 is then configured to form low friction zone 112.

The first ply 114 may comprise any number of commonly available materials chosen based on certain desirable characteristics, including durability, breathability, cost, ease of manufacture, elasticity or any other desirable characteristic. The first ply 114 generally has a low coefficient of friction when interfaced with Polytetrafluoroethylene. Elasticity is often a desirable characteristic to promote relatively free movement of the first ply 114 with respect to the partial second ply 119. This relative free movement of the first ply 114 with respect to the partial second ply 119 can help facilitate the low friction interface 117. The first ply 114 forms a relatively low friction interface with the partial second ply 119 and a relatively high friction interface with the third ply 122. The first ply 114 is often joined to the third ply 122 only near their perimeters.

The third ply 122 comprises a low cost polyester mesh material such as jersey mesh. However any suitable material may be used, including but not limited to materials or fabrics higher in elasticity, made from a silicon gel, or thin plastic materials such as polyurethane. The third ply 122 may also comprise a foam material, including visco-elastic foam. The first ply 114, partial second ply 119, adhesive ply 116 and third ply 122 comprise the managed friction material surface 111, which is used to construct seat cushions, garments, bedding, medical devices or other similar items.

The partial second ply 119 may be bonded to the third ply 122 with interposing adhesive ply 116. The adhesive ply 116 may be configured such that the perimeter of adhesive ply 120 is approximately the same as, or slightly lager than the perimeter 121 of partial second ply 119. In this embodiment the adhesive may be a dry melt adhesive, or other suitable adhesive. Typically polytetrafluoroethylene is difficult to bond to other surfaces without first preparing the bonding surface. Prior to bonding, the surface to be bonded can be etched using an agent such as sodium naphthalene. A heat press may be used to bond partial second ply 119 to the third ply 122 with the interposing adhesive ply 116. The first ply 114, partial second ply 119, third ply 122 and interposed adhesive 116 form a smooth managed friction material surface 111. The thickness of adhesive ply 116 used can be is approximately 0.011 inches, the thickness of the partial second ply 119 of polytetrafluoroethylene can be approximately 0.010 inches.

This managed friction material surface 111 has zones of high friction 113 and zones of low friction 112 without the need for abrasive sewn seams.

Example 3

Figure 8:
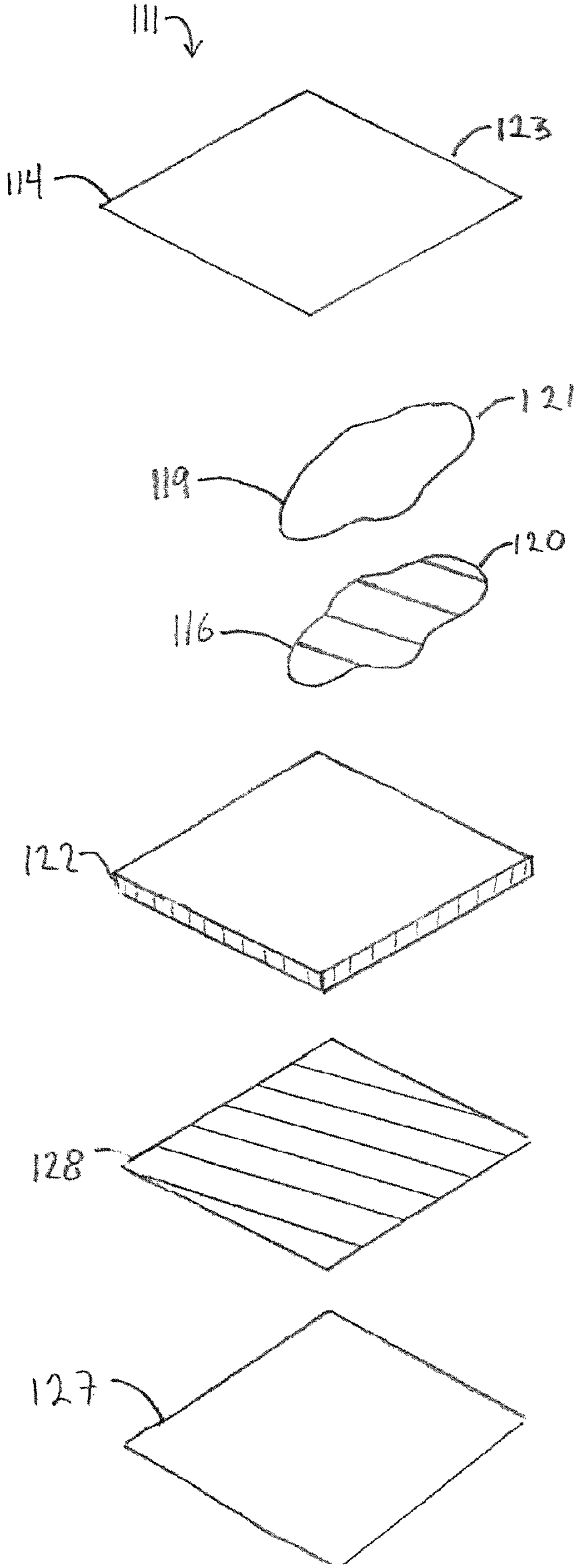
FIG. 8 is an exploded perspective view of an embodiment of the present invention with four plies.

As illustrated generally at FIG. 8, additional plies are used to form smooth managed friction material surface 111. The first ply 114 and partial second ply 119 may comprise an elastic fabric (such as Cooper style 480). One benefit of Cooper style 480 is breathability, unfortunately the breathability is severely reduced, when for example the managed friction material surface 111 is used opposite a foam cushion. Additional plies may be used to improve not only breathability, but increase friction and water resistance. The first ply 114 and partial second ply 119 are configured to form a low friction interface 117 as described previously. The partial second ply 119 is bonded with the adhesive ply 116 to a third ply 122. In this embodiment the third ply 122 comprises a spacer fabric, such as those available from the Sing Bwo Co. of Taichung City or Apex Mills of New York. A spacer fabric is loosely woven and easily passes air and water vapor. This type of material is used to provide managed friction material surface 111 with improved breathability.

Figure 9A:
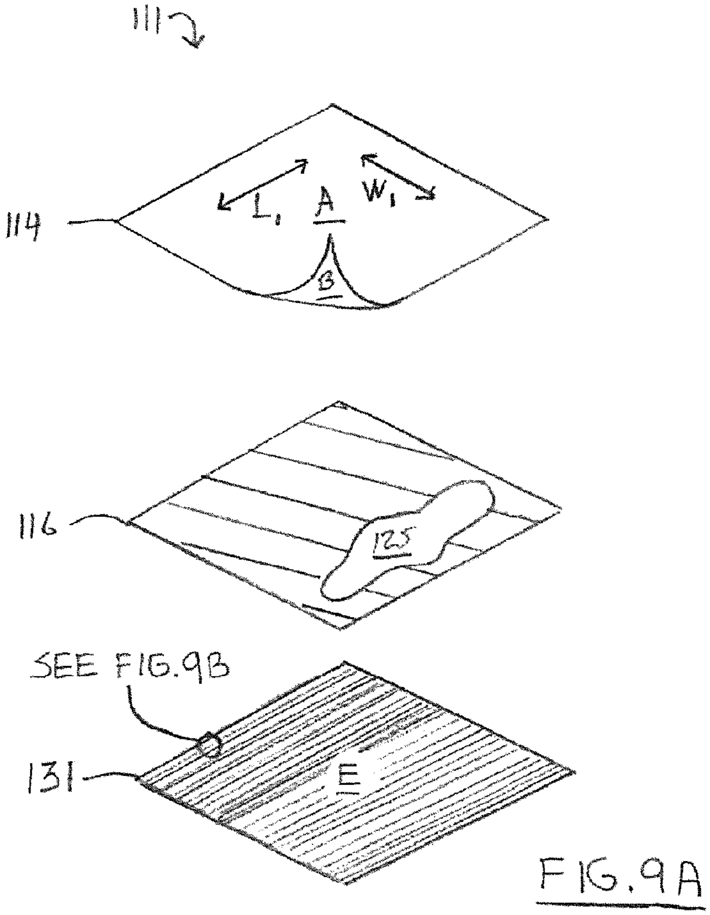
FIG. 9A is an exploded perspective view of a further embodiment of the present invention with two plies.
Figure 9B:
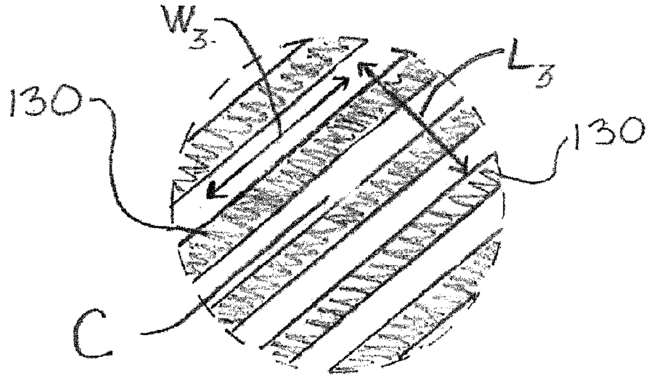
FIG. 9B illustrates a detail view of a ribbed ply.

A second adhesive ply 128 is used to bond a technical ply 127 to the third ply 122. The construction of the smooth managed friction material surface 111 can vary as will be appreciated by those skilled in the art. For example the technical ply 127 is bonded to a different ply as needed. The total number of plies may also vary. In this embodiment the technical ply 127 is bonded to the third ply 122 with a second adhesive ply 128. The technical ply provides certain desirable characteristics to the smooth managed friction material surface 111. For example the technical ply 127 is a barrier layer, comprising a thin plastic sheet, that prevents the passage of fluids such as water, human waste or other fluids. The technical ply 127 may also comprise a special high friction layer for interface with other surfaces. The technical ply 127 is also added to stiffen the third ply 122 or to make the material surface 111 more durable. The managed friction material surface 111 may also comprise a specially constructed ribbed ply 131, as shown in FIGS. 9A, 9B. The specially constructed ribbed ply 131 forms the low friction interface 117 with itself or with an elastic fabric type material.

In this embodiment a first ply 114 of elastic type material, the adhesive ply 116 and a second ribbed ply 131 are bonded to form the smooth managed friction material surface 111. As the first ply 114 has side A and side B, the ribbed ply 131 has a surface E. Surface E of ribbed ply 131 has a lengthwise direction L3 and a width wise direction W3. Surface E has specially formed ribs 130 running in the widthwise direction. In one embodiment the ribs 130 are approximately 0.005 inches in height and approximately 0.005 inches in thickness with each rib 130 running along the width W3 of surface E. The thickness and height of the ribs 130 can vary. The ribs 130 can be formed by various methods, including use of a plastic injection mold to create surface E with ribs 130. Additional methods of forming the ribs 130 on surface E includes using an etching process, or engraving the surface. Engraving is often done mechanically with a mill or laser. In this embodiment the ribbed ply 131 is injection molded from a thermoplastic Nylon 6,6 material. The bottom side of the first ply 114, side B, and the topside of the ribbed ply 131, surface E, form a low friction interface. In order for the two plies 114, 131 to form the low friction interface 117, the plies should move relatively freely in relation to each other. It is common for the coefficient of friction of this interface, depending upon material selection and environmental conditions, to be as low as 0.15.

Further, to form the interface 117, the plies 114, 131 should be oriented with each other in the following way: First, sides B and E should face each other. Second, the length L1 of the first ply 114 and the length L3 of the ribbed ply 131 should be arranged so they are perpendicular as shown in FIG. 9A and FIG. 9B. The lengths L1 of the first ply 114 can be considered the machine direction as discussed previously. The length L3 of the second ply can be considered the direction perpendicular to the greatest length of the ribs 130, in other words the ribs 130 run in a widthwise direction. The ribbed ply 131 is bonded to the first ply 114 by an adhesive ply 116 with an area of adhesive removal 125 as discussed previously throughout this application.

Example 4

Figure 10A:
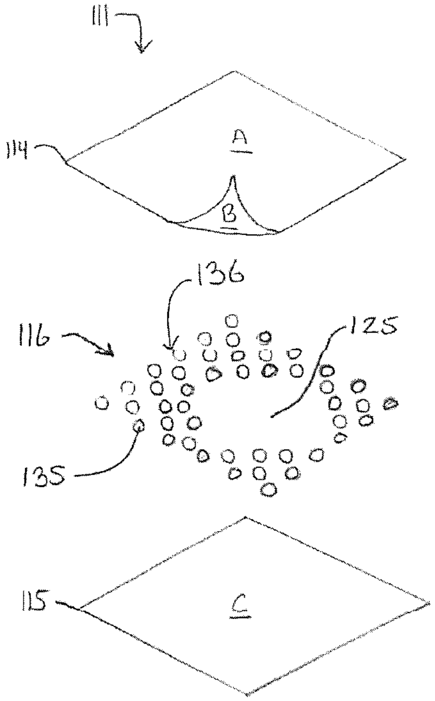
FIG. 10A is an exploded perspective view of a further embodiment of the present invention with two plies.
Figure 10B:
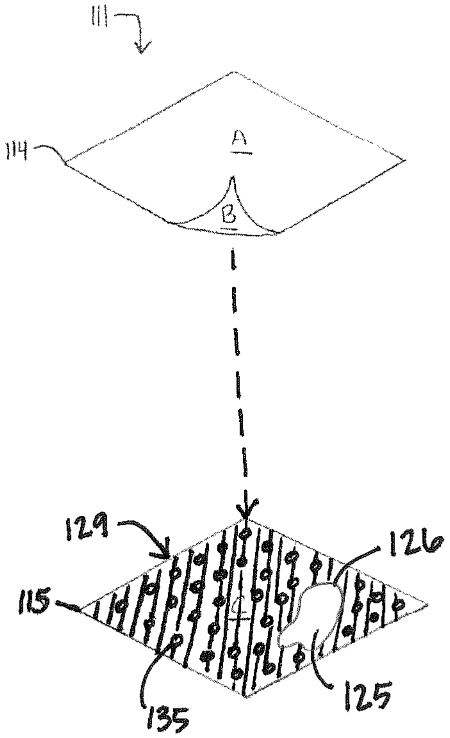
FIG. 10B is an exploded perspective view of the embodiment illustrated in FIG. 10A showing the bonded and unbonded areas of the present invention with two plies.

As illustrated generally at FIG. 10, the managed friction material surface 111 comprises the first ply 114, the adhesive ply 116 and the second ply 115. The first ply 114 and second ply 115 comprise elastic type fabrics. The first ply 114 and second ply 115 are configured as described previously to form the low friction interface 117. The interposing adhesive ply 116 bonds the first ply 114 to the second ply 115. In this embodiment the adhesive ply 116 comprises multiple adhesive dots 135. Adhesive dots 135 can be small circularly shaped areas of adhesive as shown in FIG. 10. The adhesive also dots may comprise various shapes. Small circular shapes are chosen here for their relative ease of manufacture, however the shape of dots is not limited. Adhesive dots are applied to the first ply 114 and/or to the second ply 115. The adhesive dots 135 are applied with a spray adhesive and mask adapted to allow adhesive to impinge upon desired areas only, however the adhesive may be applied in any suitable method. The spray adhesive used will vary depending on the specific material from which the low friction interface is formed. In this embodiment, Super 77. Spray Adhesive made by the 3M Corporation is used. After application, there may be dense areas of adhesive dots 136 and sparse areas of adhesive dots, such as the area of adhesive removal 125.

In FIG. 10 the adhesive dots are shown separate from the first ply 114 and the second ply 115, but the adhesive dots are typically applied onto a ply. In this embodiment the adhesive dots 135 are applied to side C of the second ply 115. After application of the spray adhesive, the first ply 114 is placed opposite the second ply 115. Bonding is accomplished per the adhesive manufacturer's instructions. After bonding, the first ply 114 and second ply 115 are not allowed to move freely with respect to one another in all areas. The greater the density of adhesive dots 135 the less freely the plies can move which generally corresponds to the high friction zone 113. In areas where adhesive dots 135 are less dense, the plies are allowed to move relatively freely with respect to one another. Adhesive dots 135 are less dense proximate the area of adhesive removal 125 which generally corresponds to low friction zone 112. In this manner, many zones of high friction 113 and zones of low friction 112 are formed. Generally the greater the density of adhesive dots 135 the less freely the plies can move and the higher the perceived coefficient of friction between the plies. Bonding in this manner forms a very smooth managed friction material surface with zones of high friction 113 and zones of low friction 112.

Example 5

Figure 11:
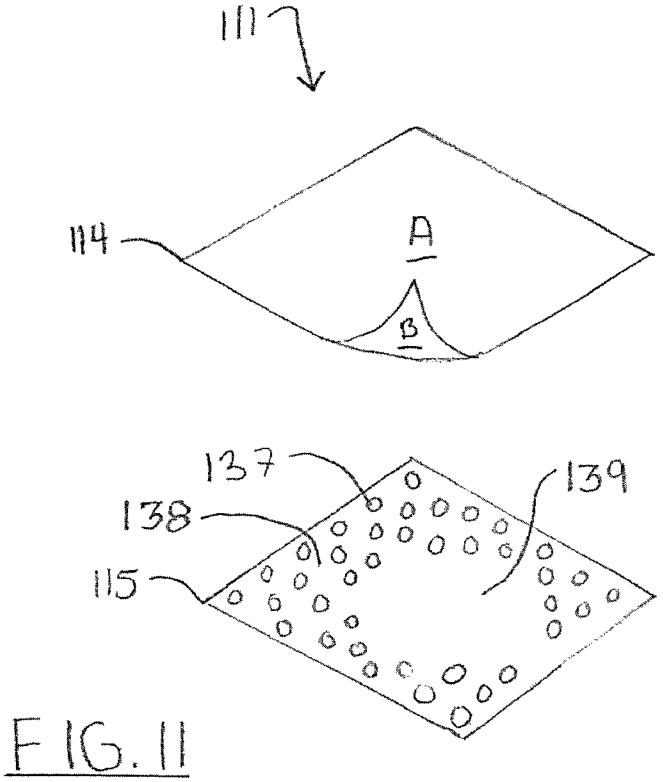
FIG. 11 is an exploded perspective view of a further embodiment of the present invention with two plies.

As illustrated generally at FIG. 11, the managed friction material surface 111 comprises a first ply 114 and a second ply 115. The first ply 114 and second ply 115 comprise the flexible type material (Cooper style 480 material). The first ply 114 and second ply 115 are configured to form a low friction interface 117 as described above. The first ply 114 is bonded to the second ply 115. Bonding of the first ply 114 to the second ply generally occurs proximate bonding areas 137. Although the bonding areas are shown only on the second ply 115 in FIG. 11 it should be understood that the bonding areas represent the configuration of bonds between the first ply 114 and the second ply 115. Although the bonding areas 137 may comprise various different configurations, the bonding areas 137 in this embodiment comprise a series of small circular areas approximately 0.25" in diameter. The bonding areas can be somewhat smaller or much larger; some users 600 may prefer a smaller diameter bonding areas 137 for comfort.

The first ply 114 and the second ply 115 can be bonded using heat and pressure, including but not limited to, use of an ultrasonic sealing machine with a custom horn configured to create the bonded areas 137 or use of a heat-sealing machine configured to create the bonded areas 137. With a heat-sealing machine, little pressure is required to create a satisfactory bond, perhaps as little as a few pounds per square inch. The temperature of the heat sealing machine may vary based on the materials used and the bond time, however in this embodiment the plies were heated for approximately 25 seconds at 425 degrees Fahrenheit.

When the first ply 114 and the second ply 115 are bonded, they are adhered proximate the bonded areas 137. In areas 137 of dense bonding 138 the plies move less freely. In areas where the bonding area 137 is less dense 139, the plies move more freely. Thus, the less dense area 139 generally corresponds to a low friction zone 112 and dense area 138 generally corresponds to the high friction zone 113. In this manner many zones of high friction 113 and zones of low friction 112 are formed on the surface 111. In this embodiment, even in the dense area 138 some space remains between the bonding areas 137, allowing the managed friction material surface 111 to retain some elasticity.

In an alternative embodiment, bonding as generally described throughout this specification can additionally be used to reinforce sewn seams as well as prevent bunching of materials. Low friction fabrics and/or materials are generally prone to bunching or distortion, especially when machine sewn, so an adhesive is used to reinforce the layers when sewing.

Figure 12:
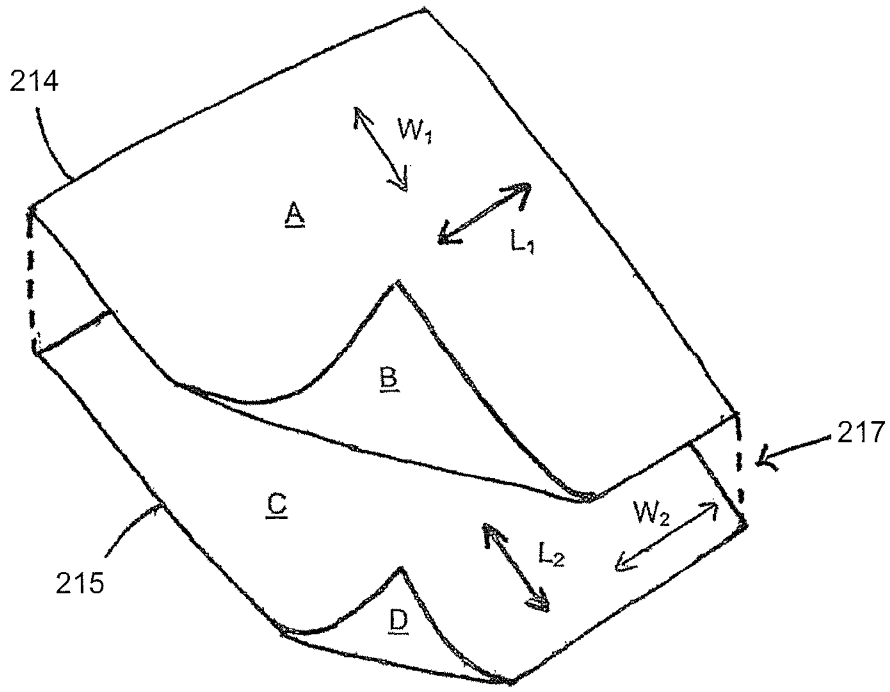
FIG. 12 is an exploded perspective view of a further embodiment of the two ply low friction interface.
Figure 13:
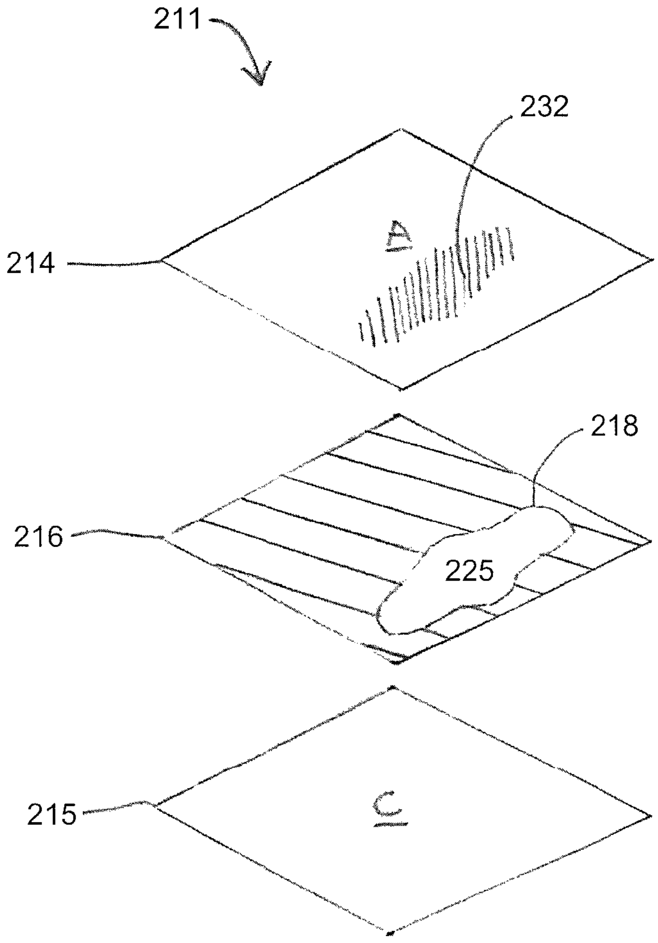
FIG. 13 is an exploded perspective view of a further embodiment of the two ply low friction interface.
Figure 14:
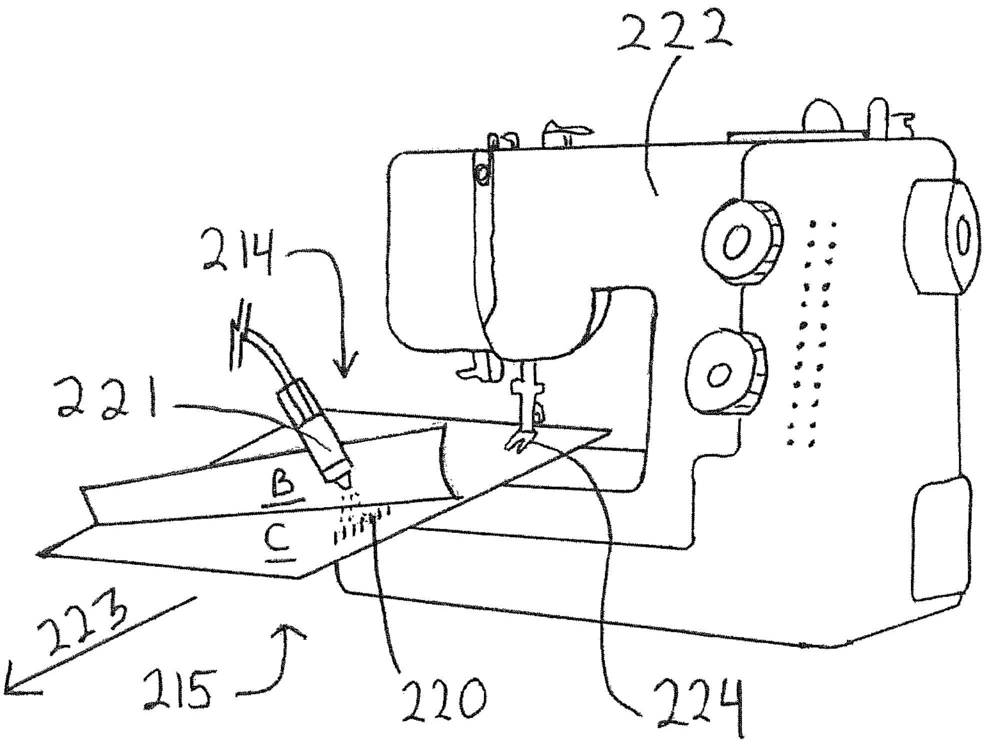
FIG. 14 is a perspective view of an embodiment of the present invention.

As Illustrated generally at FIG. 12-14, the adhesive layer, or bonding agent, 216 is applied before sewing two plies of fabric 214 and 215. More specifically, the bonding agent 216 may be applied by spray gun, roller or other suitable methods 221, to a desired area 220 of layers 214 and 215 of properly oriented fabric (Cooper style 480) as discussed previously throughout this specification. The adhesive layer 220 may be applied to the entire surface area of plies 214 and 215, or alternatively may be selectively sprayed or rolled 221 to only the area where sewing or other stitching is to occur.

In this embodiment a water-soluble adhesive is used. The adhesive, or bonding agent, comprises a mixture of water and Elmer's Glue-All in approximately a 1:1 ratio. A HVLP spray gun suitable for waterborne paints is used with a 2.0 mm nozzle and a pressure setting of 40 psi to apply the adhesive mixture. Typically 10 oz of adhesive mixture comprising 5 oz of adhesive and 5 oz of water are applied to two plies of fabric with an overlapping surface area of approximately 450 square inches. Once the adhesive is applied, the adhesive covered layer(s) 214 and/or 215 are dried at approximately 140° F. for approximately 1.5 hours prior to sewing.

Sewing and joining of the two plies 214 and 215 becomes easy after the bonding agent 216 has dried and the plies 214 and 215 have become substantially rigid. A seam 218 can then be sewn or otherwise stitched. After sewing the plies, the bonding agent or adhesive is dissolved by washing the assembled and/or sewn material in hot water, and can be done in a standard household washing machine. After washing, the stitched reinforcement of surface remains as needed and the adhesive 216 is completely removed. However, the adhesive may also be removed selectively to form low friction areas 212 as desired by selective rinsing and washing. Further, the adhesive 216 as used in this method need not be as flexible as adhesive used in bonding without stitching as the adhesive prevents bunching of the low friction material due to feeding through the sewing machine. The adhesive can also add structural reinforcement to the seam(s).

The adhesive itself may be soluble or dissolvable such that the adhesive may be removed completely or selectively removed after the first and second plies have been sewn or otherwise secured. Other suitable adhesives may not be soluble or dissolvable, but then are applied only in narrow enough areas along the intended stitch line, seam, or bonded area as to be unobtrusive when compared to the stitch width and remain in place after sewing or otherwise joining the plies of fabric. Further, the adhesive 216 applied proximate a cut or otherwise unfinished edge of a ply of fabric 214 or 215 will prevent the fabric or layer from fraying and/or unraveling.

In one embodiment adhesive remains in place after stitching. The adhesive is applied to one or both of two plies 214 and 215 in close proximity 220 to the stitching head 224 of the sewing machine 222. The direction of the machine is illustrated by arrow 223. The adhesive might be applied by spraying a fast drying adhesive or using a roll of pressure sensitive adhesive 221.

A further alternative embodiment includes bonding two plies 114 and 115 or 214 and 215 of material in and selectively dissolving areas of low friction 117 and 217 strategically. This method can be utilized with or without further reinforcement such as stitching or sewing as disclosed previously. Two plies 114, 214 and 115, 215 are positioned and then secured or bonded according to any embodiment described previously throughout the specification. Strategic bonded areas are dissolved by clamping the material surface 111 between a first and second chamber (not shown) containing an adhesive solvent.

The first chamber may be a vacuum chamber and the second chamber a solvent vapor chamber, such that the solvent flows from one chamber to the other while dissolving the adhesive ply 116, 216 interposed between plies 114 and 115 or 214 and 215 respectively, selectively between chambers. Alternatively, the second chamber may comprise a drain chamber while the first chamber comprises a liquid solvent dispenser. In either embodiment, the first and second chambers seal sufficiently to the surface 111 such that the seal (not shown) prevents intrusion of the solvent into areas of the surface 111 where adhesive is intended to remain. The areas where the adhesive has been removed 125, 225 are thus low friction areas 112, 212 and the areas where the adhesive remains are high friction areas 113, 213. The solvent used is compatible with the base materials, the fabric comprising the plies 114, 115, 214 and 2154 in which are bonded to form the low friction interface (in this example, Cooper Style 480 (80% Nylon, 20% Spandex)) as disclosed previously.

The cushion 100 and the smooth managed friction material surface 111 described throughout this specification may comprise bonded areas by various means, stitched and reinforced areas or both. The bonded areas are generally placed proximate critical areas of the user's anatomy when in use and the stitched and reinforced areas as described previously would be placed remotely from critical areas of the user's anatomy, when the user is in contact with the cushion 100 or material surface 111.

Any of the embodiments described herein including a smooth managed friction material surface may take the form of a cover for a cushion, a cover for bedding, a garment or a medical device, such as a prosthetic socket liner. The smooth managed friction material surface could comprise one part of a larger assembly or manufacture. For example only one portion of a garment may employ a smooth managed friction material surface. The use of materials is not limited to the uses disclosed herein. A smooth managed friction material surface comprises bonded plies to form a smooth material surface with at least one low friction zone.

Many other configurations for smooth managed friction material surfaces are possible. Zones of various dimensions, shapes, and locations may be used. Further, any suitable assembly schemes and/or plurality of plies may be used to achieve a desired surface. For example, a technical ply may be bonded to the first ply, or some plies may be bonded while others are attached by more conventional methods including by not limited to stitching, sewing or other suitable means.

For example, while suitable sizes, materials, fasteners, and the like have been disclosed in the above discussion, it should be appreciated that these are provided by way of example and not of limitation as a number of other sizes, materials, fasteners, and so forth may be used without departing from the scope of the invention.

Although the present invention has been described with reference to preferred embodiments, workers skilled in the art will recognize that changes may be made in form and detail without departing from the spirit and scope of the invention.

What is claimed:

1. A substantially smooth managed friction material surface for preventing abrasion or decubitus ulcers in a living being, said managed friction material surface comprising:

a plurality of plies, each ply having a smooth side;

a first frictional zone;

a second frictional zone;

at least one adhesive ply interposed partially between adjacent plies;

wherein the at least one adhesive ply is applied selectively between a first ply and a second ply of the plurality of plies and wherein when bonded, the first ply and the second ply are secured and movement restricted only where the at least one adhesive ply is interposed; and wherein when the first ply and second ply of the plurality of plies are selectively bonded at the at least one adhesive ply, the plurality of plies form a first frictional zone of higher friction and wherein the plurality of plies remain unbonded proximate the first frictional zone to form a second frictional zone of lower friction and wherein the adjacent plies are allowed to move substantially freely with respect to one another in the second frictional zone of lower friction.

2. The material surface of claim 1 where in the second ply is substantially smaller than the first ply and the first and second ply are selectively bonded.

3. The material surface of claim 2 and wherein a third ply is also selectively bonded to the first ply outside of an area where the second ply is positioned to the first ply the material surface then having the first and second frictional zones.

4. The material surface of claim 1 wherein the first ply and the second ply are positioned with respective smooth sides facing one another and wherein the first ply is positioned perpendicularly to the second ply with respect to a machine direction of a ply.

5. The material surface of claim 1 wherein the at least one adhesive ply is applied between the first and the second adjacent plies and then selectively removed after application to form a surface wherein the first ply and second ply are unbonded and allowed to move freely with respect to one another only where the adhesive ply was removed.

6. The material surface of claim 1 wherein the plurality of plies further comprises a technical ply and an additional adhesive ply interposed between the first ply and the second ply and further selectively bonded.

7. The material surface of claim 1 wherein the adhesive ply comprises a dissolvable adhesive.

8. The material surface of claim 1 wherein the first and second ply comprise a material consisting of 85% nylon and 15% spandex.

9. The material surface of claim 1 wherein the bonded and unbonded areas are positioned adjacent to one another on the material surface and the material surface remains seamless.

10. A substantially smooth managed friction material surface for preventing abrasion or decubitus ulcers in a living being, said managed friction material surface comprising:

a first of ply of material having a smooth side;

a second ply of material having a smooth side;

a first frictional zone;

a second frictional zone;

an adhesive ply wherein the adhesive ply is applied selectively between the first ply and the second ply and wherein when bonded the first ply and the second ply are secured and movement restricted only where the adhesive ply is interposed; and wherein the first and second plies are selectively bonded by the adhesive ply to form a first frictional zone, the first zone having greater friction than a second zone, and wherein the plurality of plies remain unbonded proximate the first frictional zone to form the second frictional zone, the second frictional zone having lower friction and wherein adjacent plies are allowed to move substantially freely with respect to one another in the second frictional zone.

11. The material surface of claim 10 wherein the first ply and the second ply are positioned with the respective smooth sides facing one another and wherein the first ply is positioned perpendicularly to the second ply with respect to a machine direction of a ply.

12. The material surface of claim 11 wherein the first and second ply are selectively bonded to one another by an adhesive to form a seamless surface comprising bonded and unbonded areas proximate one another.

13. The material surface of claim 12 wherein a soluble adhesive layer is applied to the first and second ply for stability and wherein the first and second ply are then machine stitched at a seam and the adhesive then dissolved at said seam.

14. The material surface of claim 10 wherein the first and second ply comprise a material consisting of 85% nylon and 15% spandex.

15. The material surface of claim 10 wherein the first ply comprises a material consisting of 85% nylon and 15% spandex and the second ply comprises a ribbed nylon.

16. An apparatus for placement on a support surface between the support surface and a living being, the living being having a bony prominence, the apparatus comprising:

a substantially smooth and seamless material surface having a plurality of zone comprising:

a first zone, wherein the first zone is a bonded zone, the bonded zone having a high coefficient of friction, the bonded zone configured for positioning remote the bony prominence; and a second zone, wherein the second zone is an unbonded zone adjacent the bonded zone, the unbonded zone having a low coefficient, the unbonded zone configured for positioning proximate the bony prominence;

wherein the bonded zone and the unbonded zone occupy different areas on a same side of a material surface and wherein no seam exists on the material surface between the adjacent zones; and wherein the zones of the material surface are selectively bonded such that adhesive is interposed and bonded only in the first zone and no adhesive is interposed and bonded at the second zone.

17. The apparatus of claim 16 wherein the material surface further comprises a first material ply and a second material ply, the first material ply positioned perpendicular to the second material ply with respect to a machine direction of a ply.

18. The apparatus of claim 17 wherein the material surface further comprises an adhesive ply interposed between the first ply and the second ply and wherein the adhesive ply is selectively interposed between the first and the second ply.

* * * * *